(12) United States Patent
Yacoby

(10) Patent No.: US 6,891,925 B2
(45) Date of Patent: May 10, 2005

(54) METHOD TO DETERMINE THE THREE-DIMENSIONAL ATOMIC STRUCTURE OF MOLECULES

(75) Inventor: Yizhak Yacoby, Bizaron (IL)

(73) Assignee: Yissum Research Development, Jerusalem (IL)

( * ) Notice: Subject to any disclaimer, the term of this patent is extended or adjusted under 35 U.S.C. 154(b) by 0 days.

(21) Appl. No.: 10/373,651

(22) Filed: Feb. 24, 2003

(65) Prior Publication Data

US 2004/0165698 A1 Aug. 26, 2004

(51) Int. Cl.[7] .............................................. G01N 23/201
(52) U.S. Cl. .............................. 378/86; 378/70; 378/71; 378/73
(58) Field of Search .............................. 378/53, 70, 71, 378/73, 86

(56) References Cited

U.S. PATENT DOCUMENTS 6,430,256 B1 * 8/2002 Yacoby ....................... 378/71

* cited by examiner

Primary Examiner—Edward J. Glick
Assistant Examiner—Courtney Thomas
(74) Attorney, Agent, or Firm—Martin Fleit; Paul D. Bianco; Fleit Kain Gibbbong Gutman Bongini & Bianco, P.L.

(57) ABSTRACT

The invention presents an x-ray method for determining the three-dimensional molecular structure of molecules having an unknown structure. The molecules having unknown structure are arranged in a two-dimensional periodic array on a substrate molecular crystal having a known structure. It is a requirement of the method that the dimensions of the molecules with the unknown structure are smaller than the corresponding dimensions of the substrate crystal unit cell.

1 Claim, 3 Drawing Sheets

US 6,891,925 B2

METHOD TO DETERMINE THE THREE-DIMENSIONAL ATOMIC STRUCTURE OF MOLECULES

FIELD OF THE INVENTION

The present invention relates to determining molecular structure using x-ray techniques. More specifically the invention relates to an x-ray method for determining the three-dimensional molecular structure of molecules arranged in a two-dimensional periodic array on a substrate molecular crystal having a known structure.

BACKGROUND OF THE INVENTION

Knowledge of the three-dimensional atomic structure of molecules is essential in understanding their function as well as in designing new industrial pharmaceutical and agricultural materials. A number of existing methods of determining molecular structure are based on x-ray diffraction methods that determine both the amplitude and the phase of the diffraction. They all study the structure of 3 dimensional crystals composed of the molecules of interest and yield good results. The main difficulty with these methods is the need to crystallize the molecules into a 3 dimensional crystal. The process of crystallization is molecule specific, namely, the conditions needed to crystallize different molecules are different and the right conditions for crystallization need to be determined for each type of molecule individually. Many molecules in particular those residing in cell membranes are very difficult or impossible to crystallize at present.

The structures of molecules crystallized as two dimensional crystals have also been studied by transmission electron microscopy. This method provides a quite limited resolution on the order of a few angstroms and, as in all of the other prior art methods, the process of crystallization is the bottle-neck for the investigation of the molecular structure because it is molecule specific. In fact there exist many molecules of interest for which a method of crystallization has not been perfected. Crystallizing a molecule is usually the most difficult part of the structure determination procedure and, therefore, it would be highly desirable if a method could be provided for determining the three-dimensional structure of large molecules, such as biological or chemical molecules, that avoids the necessity of crystallizing the molecules.

It is therefore an object of the present invention to provide a method for determining the three-dimensional atomic structure of large molecules such as biological or chemical molecules.

It is another object of the present invention to provide a method for determining the three-dimensional atomic structure of large molecules such as biological or chemical molecules without the need of crystallizing the molecules.

Further purposes and advantages of this invention will appear as the description proceeds.

SUMMARY OF THE INVENTION

The present invention provides an x-ray method for determining the three dimensional atomic structure of large molecules such as biological or chemical molecules that are arranged on the surface of a substrate crystal composed of molecules having a known structure. The dimensions of the molecules with the unknown structure must be smaller than the corresponding dimensions of the substrate crystal unit cell.

According to the method of the invention, it is therefore possible to determine the structure of the unknown molecules without the need for crystallizing them. The unknown structure of the molecules is determined from the measured x-ray properties of the system and the known atomic structure of the substrate crystal.

The method of the invention comprises the following steps:

measuring the x-ray scattering intensity;

determining, from the measured x-ray scattering, and the known complex scattering factors (CSFs) of the substrate the CSFs of the two dimensionally periodic layer of unknown molecules and the CSFs of the entire system composed of the molecular layer and the substrate molecular crystal;

determining the electron density of the molecules that are arranged in the two-dimensional periodic array from the CSFs of the two-dimensional periodic array; and determining, from the electron density, the unknown atomic structure of the molecules that are arranged in the two-dimensional periodic array.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

Figure 1A:
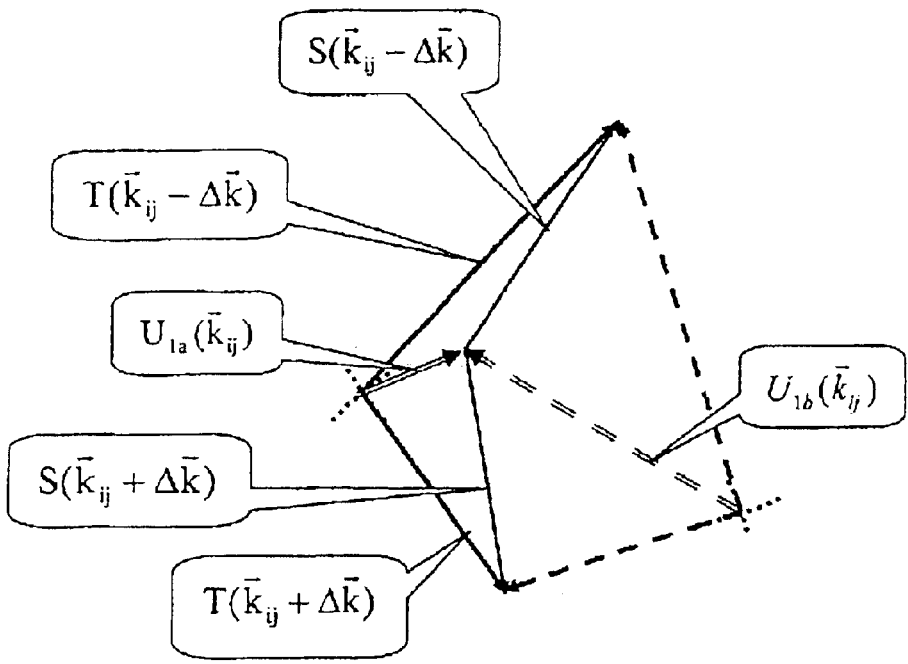
FIGS. 1A and 1B schematically illustrate equations 1 and 2 and their solutions.

The theoretical/computational basis for the present invention is found in U.S. Pat. No. 6,430,256 by the same inventor, the description of which, including references cited therein, is incorporated herein by reference in its entirety.

In the present invention, the molecules with the unknown structure are attached to the surface of a crystal whose atomic structure is known. The molecules are attached in a unique way such that an atomically accurate periodic array in two dimensions is formed. It is a necessary condition of the method of the invention that all dimensions of the molecules with the unknown structure are smaller than the corresponding dimensions of the substrate crystal unit cell. This condition is the result of the requirement that the unknown molecules, when attached to the substrate crystal, do not touch each other. If these conditions are satisfied by the system, then the method of the invention is applicable to any type of molecules attached to any type of crystal in any possible way.

The system composed of the substrate crystal and the molecular layer on top of it is periodic in two dimensions and a periodic in the third.

Consequently the Fourier transform of the system electron density is non-zero along lines in reciprocal space known as the Bragg rods. The Fourier transform along the Bragg rods contains all of the information about the system structure. At any point along the Bragg rods, the Fourier transform of the electron density is proportional to the x-ray complex scattering factor (CSF). Thus back Fourier transforming the CSFs provides the system electron density and its atomic structure. Usually the intensity of the x-ray scattering, which is proportional to the absolute value squared of the CSF, is measured. In the method of the present invention, the phase is also determined and, from the phase and the intensity of scattering, the CSFs are determined.

At any point along a Bragg rod the CSF is the complex sum of two components, the CSF of the truncated crystal and the CSF of the molecular layer that is attached to the planar surface of the substrate crystal. The first CSF is known, because of the basic condition that the structure of the truncated crystal is known, while the second CSF is unknown.

Due to the fact that the molecular dimension in the direction perpendicular to the surface is small compared to the dimensions of the corresponding crystal unit cell, the spacing between points along a Bragg rod that are needed to fully obtain the structure is larger or equal to the spacing between two consecutive bulk crystal Bragg peaks. Therefore it is sufficient to determine the CSFs of the molecular layer at the positions along the Bragg rods corresponding to the substrate Bragg points.

Consider now two points along a Bragg rod, one on each side of the Bragg peak say at +/−0.1 of the distance between two consecutive Bragg points. Then at each point:

$$S(\vec{k}_{ij}-\Delta\vec{k})+U(\vec{k}_{ij}-\Delta\vec{k})=T(\vec{k}_{ij}-\Delta\vec{k})$$

$$S(\vec{k}_{ij}+\Delta\vec{k})+U(\vec{k}_{ij}+\Delta\vec{k})=T(\vec{k}_{ij}+\Delta\vec{k}) \quad (1)$$

Here, $\vec{k}_{ij}$ is the reciprocal space vector of the $i^{th}$ Bragg point on the $j^{th}$ Bragg rod, and S, U, and T are the CSFs of the truncated crystal, the unknown molecular layer and the entire system respectively. Note that $S(\vec{k}_{ij}-\Delta\vec{k})$ and $S(\vec{k}_{ij}+\Delta\vec{k})$ are very different from each other because their phases differ approximately by $\pi$. On the other hand $U(\vec{k})$ varies slowly with $\vec{k}$ so $U(\vec{k}_{ij}-\Delta\vec{k})$ and $U(\vec{k}_{ij}+\Delta\vec{k})$ can be approximated as being equal. Taking the absolute value of equation 1 yields:

$$|S(\vec{k}_{ij}-\Delta\vec{k})+U(\vec{k}_{ij})|=|T(\vec{k}_{ij}-\Delta\vec{k})|$$

$$|S(\vec{k}_{ij}+\Delta\vec{k})+U(\vec{k}_{ij})|=|T(\vec{k}_{ij}+\Delta\vec{k})| \quad (2)$$

The values of $|T(\vec{k}_{ij}+\Delta\vec{k})|$ and $|T(\vec{k}_{ij}-\Delta\vec{k})|$ can be measured at all i, j points in the usual way, which is well known to the skilled person.

Figure 1B:
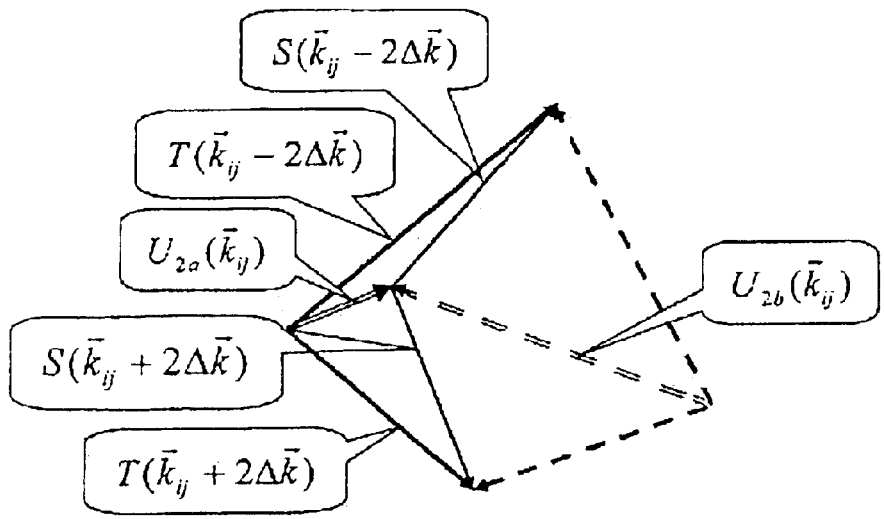

Thus in these equations S is known and |T| is measured, therefore they can be solved for the complex unknown U. These equations and their solutions are schematically illustrated in FIGS. 1A and 1B. The representation of equation 1 for $\Delta\vec{k}$ is shown in FIG. 1A. The CSFs of the truncated crystal (S) are known. The absolute values of the total CSFs (indicated by the single dashed lines) are experimentally measured. These determine the unknown CSF of the molecular layer (indicated by the double solid lines). It is to be noted that the above procedure yields two solutions $U_{1a}(\vec{k}_{ij})$ and $U_{1b}(\vec{k}_{ij})$ only one of which is correct. The double dashed lines represent the second possible solution.

To find the correct solution the above procedure is repeated with $2\Delta\vec{k}$ (shown in FIG. 1B) and the two pairs of solutions are compared. The correct solutions in both pairs should be approximately equal to each other. In the case shown in FIGS. 1A and 1B, the correct solutions are $U_{1a}(\vec{k}_{ij}) \cong U_{2a}(\vec{k}_{ij})$. In all other pairs the members of the pair are substantially different from each other.

Simulation

To demonstrate the method of the invention, one simulation out of many that have been carried out will now be described. This simulation is provided merely to illustrate the invention and is not intended to limit the scope of the invention in any manner.

A simulated molecular crystal composed of Lck kinase molecules was constructed. Each molecule has 2378 atoms (excluding hydrogen). On its surface was placed one streptavidin monomer molecule with 882 atoms on each substrate surface unit cell. The CSFs of the substrate R, the molecular layer CSFs $U_s$, and the absolute values of the total CSFs |T| along the Bragg rods were then calculated.

The total CSFs |T| are proportional to the square root of the x-ray scattering intensities that would be experimentally measured; therefore they can be treated as simulated experimental data. Then |T| and the known CSFs of the truncated crystal R are used to obtain the CSFs of the molecular layer which is now treated as the unknown U. The absolute values and phases of U obtained in this way are shown in FIGS. 2 and 3.

Figure 2:
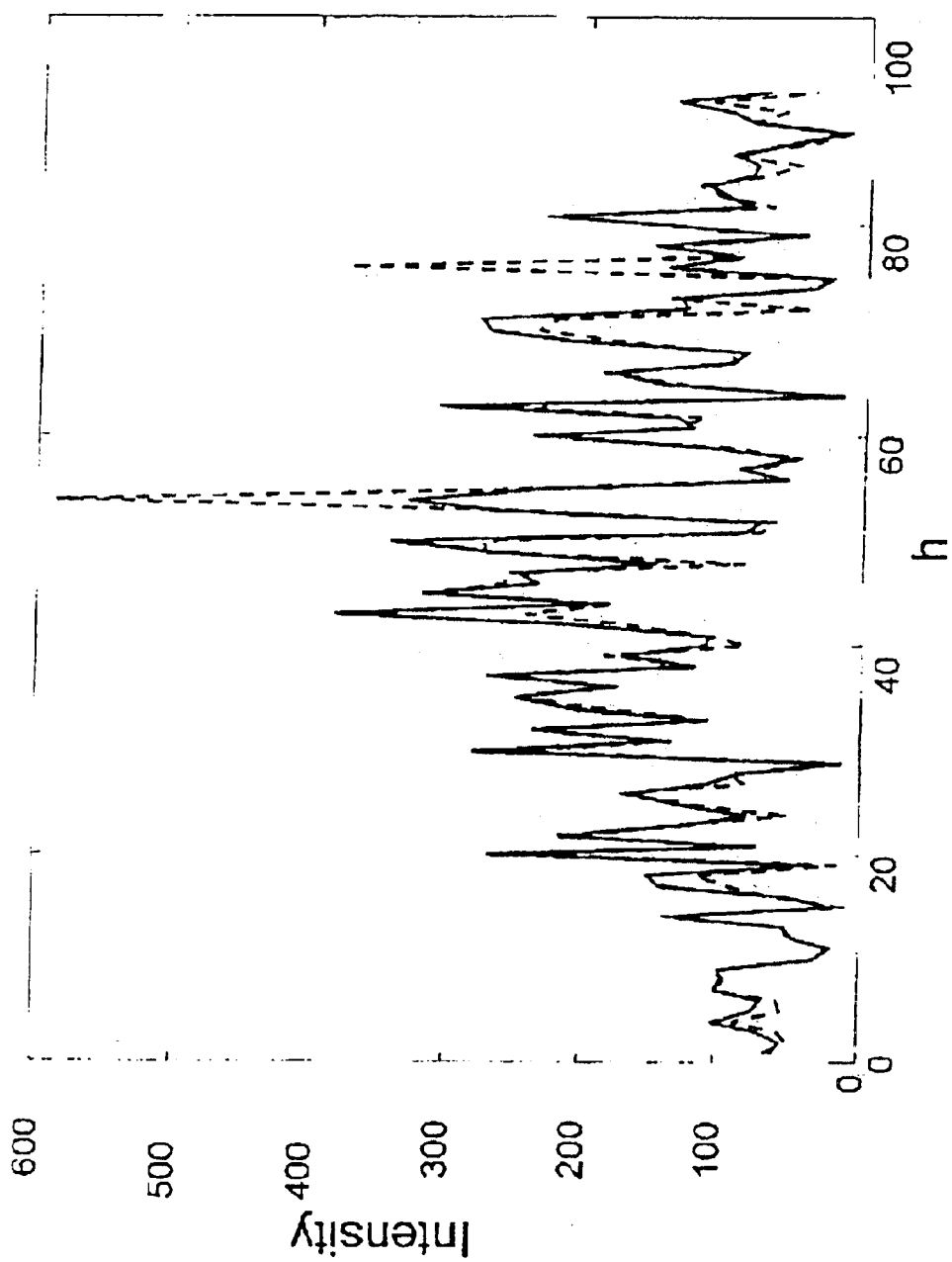
FIG. 2 shows the amplitude of the molecular layer CSFs along one of the Bragg rods.

FIG. 2 shows the absolute value of the CSFs along the (20, 15) Bragg rod as a function of position along the Bragg rod. The positions h are in units of the distance between consecutive Bragg points along the rod. The absolute value of $U_s$ (the simulated CSFs) is shown as a solid line and the absolute value of U (CSFs calculated using the method of the invention) is shown as a dashed line.

Figure 3:
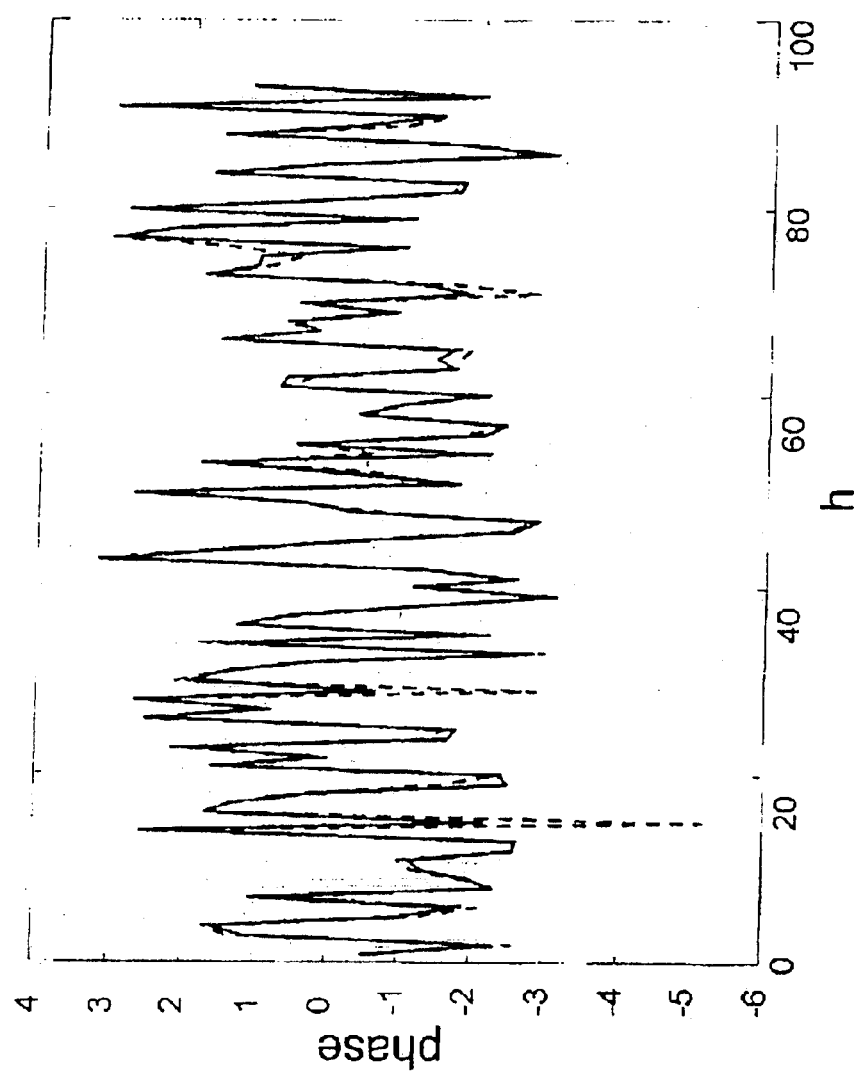
FIG. 3 shows the phase of the molecular layer CSFs along one of the Bragg rods.

FIG. 3 shows the phase of the CSFs along the (20, 15) Bragg rod as a function of position along the Bragg rod. The positions h are in units of the distance between consecutive Bragg points along the rod. The phase of $U_s$ (simulated CSFs) is shown as a solid line and the phase of U (CSFs calculated using the method of the invention) is shown as a dashed line.

It can be seen that the simulated $U_s$ and the values of U calculated using the method of the invention agree very well in both amplitude and phase. This agreement is typical of that found for all of the Bragg rods.

After determining the CSFs of the molecular layer, its electron density and atomic structure is then obtained by Fourier transformation.

Although embodiments of the invention have been described by way of illustration, it will be understood that the invention may be carried out with many variations, modifications, and adaptations, without departing from its spirit or exceeding the scope of the claims.

What is claimed is:

1. An x-ray method for determining the three-dimensional molecular structure of molecules having an unknown structure arranged in a two-dimensional periodic array on a substrate molecular crystal having a known structure, wherein the dimensions of the molecules with the unknown structure are smaller than the corresponding dimensions of the substrate crystal unit cell, said method comprising the following steps:

measuring the x-ray scattering intensity;

calculating the complex scattering factors (CSFs) of said two dimensional periodic array of said molecules with unknown atomic structure and the total CSFs of the system composed of said molecules arranged in a two-dimensional periodic array on said substrate molecular crystal from said measured x-ray scattering and the known CSF of said substrate molecular crystal;

determining, from said calculated CSF of said two-dimensional periodic array, the electron density of said molecules arranged in said two-dimensional periodic array; and determining, from said electron density, the unknown structure of said molecules arranged in said two-dimensional periodic array.

* * * * *